United States Patent [19]
Austin et al.

[11] Patent Number: 6,129,727
[45] Date of Patent: Oct. 10, 2000

[54] ORTHOPAEDIC SPATIAL FRAME APPARATUS

[75] Inventors: Ed Austin; Anthony James, both of Bartlett, Tenn.; James E. Orsak, Huntersville, N.C.

[73] Assignee: Smith & Nephew, Memphis, Tenn.

[21] Appl. No.: 09/261,660

[22] Filed: Mar. 2, 1999

[51] Int. Cl.$^7$ ........................................ A61F 5/04
[52] U.S. Cl. ........................................ 606/56
[58] Field of Search .................. 606/54, 55, 56, 606/57, 58

[56] References Cited

U.S. PATENT DOCUMENTS

| | | | |
|---|---|---|---|
| 2,391,537 | 12/1945 | Anderson | 128/84 |
| 3,985,127 | 10/1976 | Volkov et al. | 606/55 |
| 4,620,533 | 11/1986 | Mears | 128/92 |
| 4,889,111 | 12/1989 | Ben-Dov | 606/54 |
| 5,179,525 | 1/1993 | Griffis et al. | 364/512 |
| 5,180,380 | 1/1993 | Pursley et al. | 606/54 |
| 5,209,750 | 5/1993 | Stef | 606/54 |
| 5,681,309 | 10/1997 | Ross, Jr. et al. | 606/54 |

FOREIGN PATENT DOCUMENTS

| | | | |
|---|---|---|---|
| 85 01728 | 8/1986 | France | A61B 17/60 |

OTHER PUBLICATIONS

"Basic Ilizarov Techniques" *Techniques in Orthopaedics®*, vol. 5, No. 4, Dec. 1990, pp. 55–59.

S.V. Sreenivasan et al., "Closed–Form Direct Displacement Analysis of a 6–6 Stewart Platform", *Mech. Mach. Theory*, vol. 29, No. 6, pp. 855–864, 1994.

Nanua, P., Waldron, J.J., and Murthy, V., "Direct Kinematic Solution of a Stewart Platform", *Ieee Transactions on Robotics and Automation*, vol. 6, No. 4, Aug. 1990, pp. 438–443.

Fichter, E.F., "A Stewart Platform–Based Manipulator: General Theory and Practical Construction", *International Journal of Robotics Reasearch*, vol. 5, No. 2, pp. 157–182.

*Primary Examiner*—Michael Buiz
*Assistant Examiner*—Anthony King
*Attorney, Agent, or Firm*—Garvey, Smith, Nehrbass & Doody, LLC

[57] ABSTRACT

An orthopaedic fixation frame apparatus includes a pair of spaced apart support members such as circular rings, plates, or the like supported by a plurality of struts that span therebetween. One end of the struts adjacent the upper ring is provided with a position adjusting member that forms an interface between the support member and one end of the struts. The position adjusting members include joints (e.g., universal joints) for enabling angular change between the position of the struts and the support members.

34 Claims, 3 Drawing Sheets

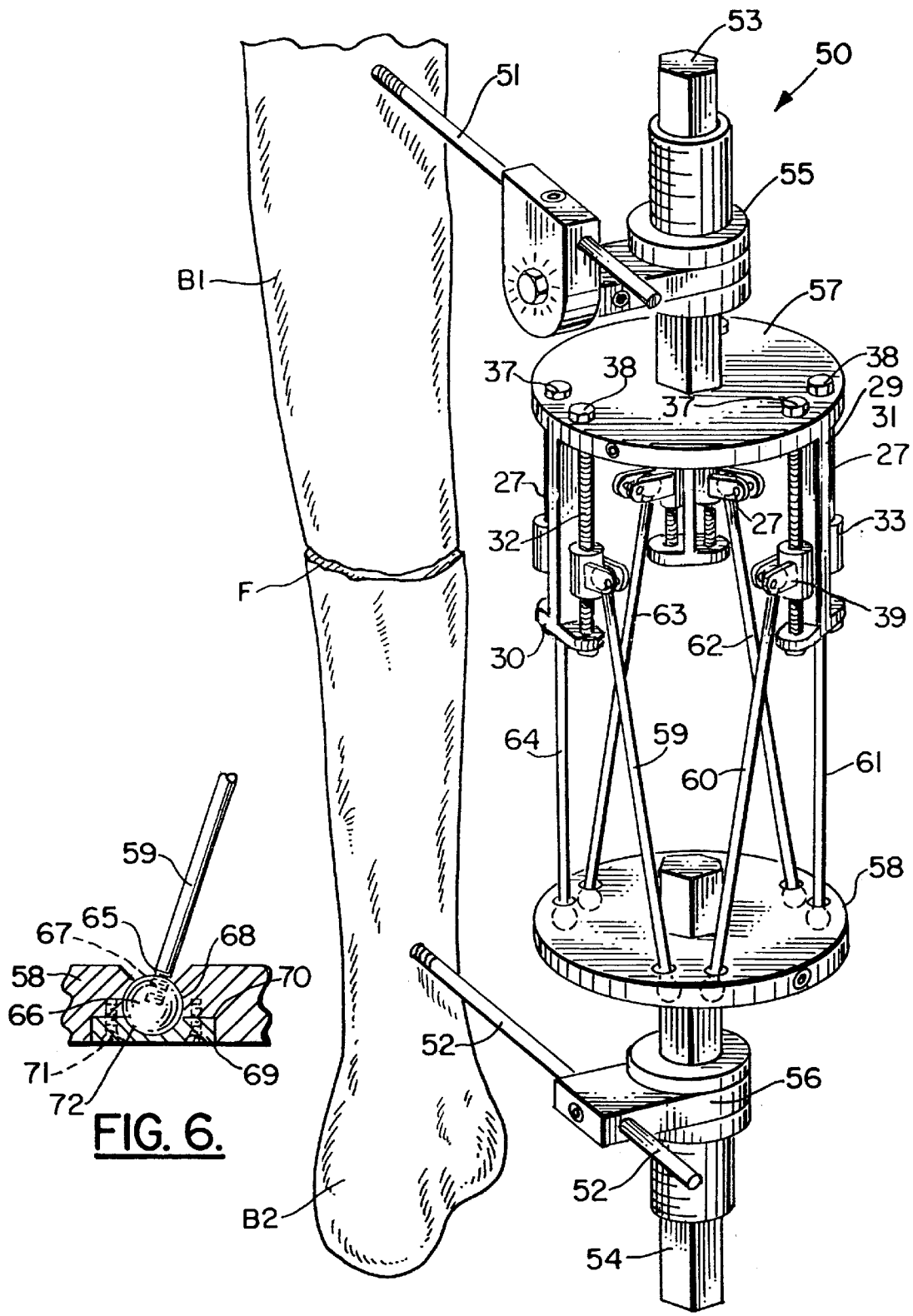

ORTHOPAEDIC SPATIAL FRAME APPARATUS

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to orthopaedic surgical fixation devices, and more particularly to an improved orthopaedic spatial frame fixation apparatus that uses a plurality of supports struts of equal length to support a pair of frame members such as plates or circular rings affixed to respective bone parts with pins. Even more particularly, the present invention relates to a spatial frame for use in orthopaedic fixation procedures wherein bone parts are supported with circular rings, plates, or the like and elongated struts spanning therebetween, one end portion of each strut having a position adjusting member that can be in the form of a bracket, threaded rod, spool, and knob that changes the distance between an end of a strut and the adjacent ring, plate or like support member.

2. General Background of the Invention

It is often necessary to realign, reposition and/or securely hold two elements relative to one another. For example, in the practice of medicine, bone fragments and the like must sometimes be aligned or realigned and repositioned to restore boney continuity and skeletal function, etc. At times this may be accomplished by sudden maneuver, usually followed by skeletal stabilization with cast, plate and screws, intramedullary devices, or external skeletal fixators.

A bone fragment can be moved, in general, from its original position as in a nonunion or malunion or from its intended position as in congenital deformities along six separate axes, a combination of three orthogonal translational axes (e.g., typical "X," "Y" and "Z" axes).

Certain boney skeletal injuries or conditions are sometimes treated with an external frame that is attached to the boney skeleton with threaded and/or smooth pins and/or threaded and/or smooth and/or beaded wires. Such constructs are commonly referred to as orthopaedic external fixators or external skeletal fixators. External fixators may be utilized to treat acute fractures of the skeleton, soft tissue injuries, delayed union of the skeleton when bones are slow to heal, nonunion of the skeleton when bones have not healed, malunion whereby broken or fractured bones have healed in a malposition, congenital deformities whereby bones develop a malposition, and bone lengthening, widening, or twisting.

External fixator frames vary considerably in design and capabilities, and may include multiple or single bars or rods, and a plurality of clamps for adjustably securing the bars to pins or wires which are, in turn, joined to the boney skeleton. The pins or wires may extend completely through the boney skeleton extending out each side of the limb or may extend through the boney skeleton and out one side of the limb. Pins which extend completely through the boney skeleton and out both sides of the limb are commonly referred to as "transfixation pins." Pins which extend through the boney skeleton and out only one side of the limb are commonly referred to as "half pins." Such external fixator frames may be circumferential for encircling a patient's body member (e.g., a patient's femur), or may be unilateral for extending along one side of a patient's body member. More that one unilateral external fixator frame can be applied to the same length of the patient's body member. Materials for frames also vary, including metals, alloys, plastics, composites, and ceramics. External fixators vary in their ability to accommodate different spatial relations between the pin and bar.

Prior art external fixators stabilize bone fragments by holding the fragments in a relatively fixed spatial relation. Some of the more completely adjustable external fixators allow the physician to reorient one fragment with respect to the other along all six axes in an acute motion, usually by loosening one or more clamps and effecting the corrective motion manually and retightening clamps to hold the fragments stably.

A circumferential external fixator system was disclosed by G. A. Ilizarov during the early 1950's. The Ilizarov system include at least two rings or "halos" that encircle a patient's body member (e.g., a patient's leg), connecting rods extending between the two rings, transfixion pins that extend through the patient's boney structure, and connectors for connecting the transfixion pins to the rings. Use of the Ilizarov system to deal with angulation, translation and rotation is disclosed in "Basic Ilizarov Techniques," *Techniques in Orthopaedics®*, Vol. 5, No. 4, December 1990, pages 55–59.

Mears, U.S. Pat. No. 4,620,533, issued Nov. 4, 1986, discloses a unilateral external fixator system including a plurality of fixation pins attached to at least one rigid bar through adjustable clamps having articulating balls which allow rotational adjustment of each pin or bar.

Stef, U.S. Pat. No. 5,209,750, issued May 11, 1993, discloses a unilateral external fixator system including an orthopaedic brace for rigidly connecting groups of pins screwed into a long bone for the reduction of a fracture of the long bone. The brace includes a telescopic support made up of an elongated tube and an elongated rod slidable within the tube. A first plate is attached to the outer end of the tube and a second plate is attached to the outer end of the rod. Third and fourth plates are adjustably attached to the first and second plates, respectively, by way of threaded rods and ball-and-socket joints. Jaws are attached to each third and fourth plate to secure the pins to the brace.

Prior art orthopaedic external fixators differ in their ability to move or adjust one bone fragment with respect to the other in a gradual fashion. Some allow gradual translation, others allow gradual rotation about two axes. The Ilizarov system can provide an external fixation frame that could provide gradual correction along and about six axes; however such a frame would require many parts and would be relatively complicated to build and use in a clinical situation.

Often orthopaedic external fixators such as Ilizarov frames must be modified later on after their initial application. Such modification may be necessary to convert from one correctional axis to another or to convert from an initial adjustment type of frame to a weight bearing type of frame, some of the correctional configurations not being stable enough for weight bearing.

More simplistic external fixators may accomplish a rotation of fragments about a center of rotation contained on the external fixator. This may or may not correspond to the center or rotation necessary to fully correct the deformity by angular correction alone. In no circumstances will a center of rotation necessary to fully correct the deformity by angular correction alone. In no circumstances will a center of rotation confined to the external fixator create a virtual center of rotation remote to the external fixator as is frequently required in the treatment of these deformities. Some orthopaedic external fixators utilize a simple hinge which cannot create a center of rotation remote to its mechanism. The Ilizarov system provides a circumferential encompassing type fixator that is more universal in that it permits the placement of the hinge axis around the bone, but does not allow rotation about an axis remote to its mechanism. A focal hinge made of an arc segment of gear or track with a following carriage can create a center of rotation remote to the mechanism but may not be applicable to certain situations where because of anatomy or preference the mechanism is to be applied to the concavity of a deformity, especially a severe deformity where there is no space to apply the long arc segment of gear or track necessary to fully correct the deformity.

Anderson, U.S. Pat. No. 2,391,537, issued Dec. 25, 1945, discloses an orthopaedic external fixator for fracture reduction including a pair of hollow tubes telescopically joined together, a plurality of pins for transfixing bone elements, a first fixation unit slidably mounted on one of the tubes for connecting a pair of the transfixion pins to that tube, and a second fixation unit attached to the end of the other tube for connecting a pair of the transfixation pins to that tube. One of the tubes is telescopically mounted within the other tube. A threaded adjusting shaft is mounted within the tubes and can be manually rotated by way of a wrench head located at the outer end of one of the tubes. Rotation of the shaft causes a nut nonrotatably located within the tubes to move longitudinally along the shaft. Coil springs located within the tubes on either side of the nut transfer longitudinal movement of the nut to the tubes while permitting a certain desired yielding and eliminating any perfectly solid and hard contact. A geared mechanism allows for correction of rotational deformity, utilizing an arc segment of gear and a mating carriage with corresponding pinion.

A "Stewart platform" is a fully parallel mechanism used in flight and automotive simulators, robotic end-effectors, and other applications requiring spatial mechanisms with high structural stiffness; and includes a base platform, a top platform, and six variable limbs extending between the base and top platforms. See S. V. Sreenivasan et al., "Closed-Form Direct Displacement Analysis of a 6—6 Stewart Platform," *Mech. Mach. Theory*, Vol. 29, No. 6, pp. 855–864, 1994.

Prior art known to Applicants does not disclose or suggest the present invention. For example, nothing in the known prior art discloses a frame that can be adjusted changing the position between a ring and a strut, wherein the struts are of a fixed length, and without requiring joints to be unclamped, etc.

BRIEF SUMMARY OF THE INVENTION

The present invention provides an improved orthopaedic fixation apparatus that is used with a pair of support members (e.g., rings or plates) that are held in spaced apart relationship with a plurality of struts. Rings and plates of this type are used, for example, in Ilizarov procedures wherein bone pins supported by the rings or plates extend to the bone tissue.

The improved spatial frame apparatus of the present invention solves the problems confronted in the art in a simple and straightforward manner. What is provided is an improved fixation apparatus that uses fixed length struts and position adjusting members that can vary the distance between a ring or plate and the struts.

In one embodiment, upper and lower rings each have a central opening, inner and outer ring surfaces, and upper and lower ring surfaces. Each of the rings provides a plurality of openings or slots that extend between the respective upper and lower ring surfaces.

A plurality of struts span between the rings to hold the rings apart in desired ring positions. A plurality of position adjusting members form an interface between one of the rings and the upper end of each of the struts.

Each position adjusting member includes a bracket or frame attached to a ring. The bracket holds a pair of threaded rods. The rods have end portions, one end portion forming a connection to a ring at a ring opening, the other end portion being positioned in between the upper and lower rings, supported by a distal end portion of the bracket.

Each position adjusting member has an articulating, universal joint portion that attaches to an end of a strut. The articulating portion threadably engages a threaded rod.

The position adjusting members are configured to increase the distance between one end of a strut and one of the rings. The struts are preferably of substantially the same length and/or fixed length members that do not change in length.

The plurality of position adjusting members vary the distance between one of a strut and the adjacent ring. The plurality of position adjusting members are positioned next to one of the rings, preferably being connected thereto.

Each of the position adjusting members can include an adjustment knob that is rotated to vary the distance between a ring and a strut. The articulating portions can include a universal joint and an internally threaded spool that is attached to the threaded rod. As the distance between one end of a strut and the ring is varied, angular displacement is automatically compensated with the universal joints.

The plurality of position adjusting members can be attached (e.g., welded) to the upper ring. In such a case, universal joints form the interface in between the lower ring and the lower end of each of the struts.

In a second embodiment, a unilateral fixator uses plates instead of rings.

In both embodiments, each position adjusting member preferably comprises a support bracket member, a pair of threaded rods, each having a continuous thread thereon, one end of the rod abutting the frame, the other end of the rod extending through one of the openings. A universal joint with an internally threaded spool or sleeve is mounted on the rod. A knob enables the user to rotate the rod, wherein the rotation of the knob and rod moves the universal joint and spool into multiple adjustment positions in between the ring and the support bracket.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 5 is a perspective view of a second embodiment of the apparatus of the present invention;

FIG. 6 is a fragmentary view of the second embodiment of the apparatus of the present invention; and FIG. 7 is another fragmentary view of the preferred embodiment of the apparatus of the present invention illustrating the universal joint type connection between a strut and the lower ring.

DETAILED DESCRIPTION OF THE INVENTION

Figure 1:
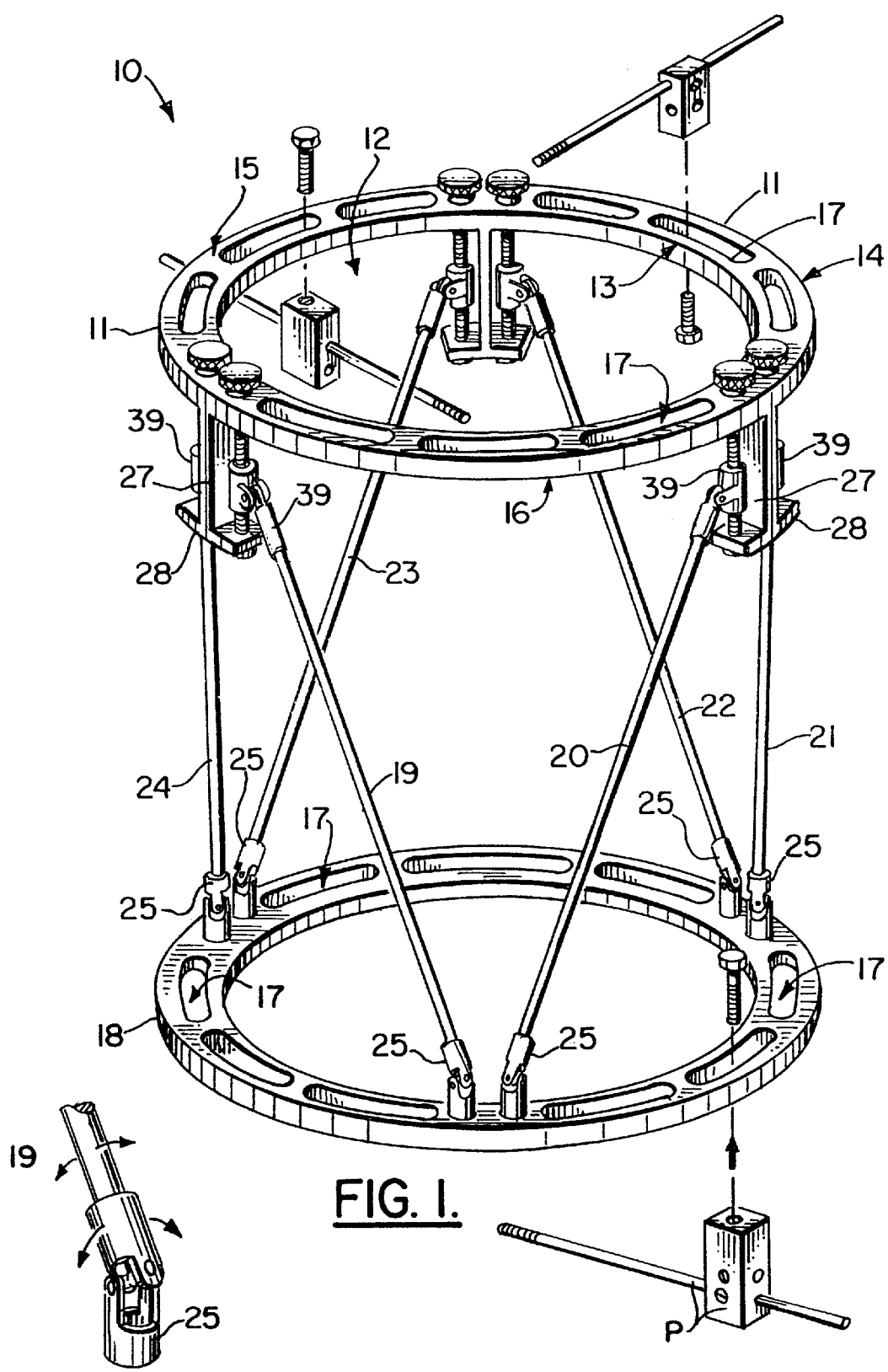
FIG. 1 is a perspective view of the preferred embodiment of the apparatus of the present invention.
Figure 2:
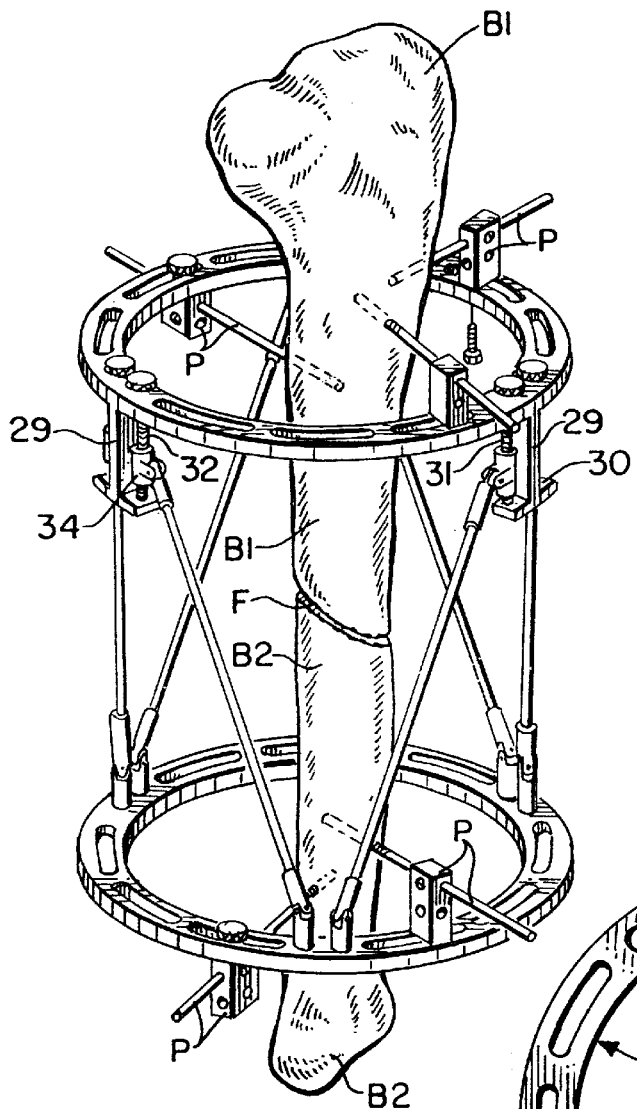
FIG. 2 is a perspective view of the preferred embodiment of the apparatus of the present invention shown mounted to a pair of bone parts.

FIGS. 1–4 and 7 show generally the preferred embodiment of the apparatus of the present invention designated generally by the numeral 10. Fixation frame apparatus 10 includes an upper ring 11 and a lower ring 18 that are held in spaced apart relation with a plurality of support struts 19–24. The upper ring 11 has a central opening 12 through which the patient's bone B can pass during surgery as shown in FIG. 2.

Ring 11 has an inner annular surface 13 and outer annular surface 14. Ring 11 has an upper flat surface 15 and a lower flat surface 16. A plurality of circumferentially spaced openings or slots 17 extend through the ring 11 in between the upper and lower surface 15, 16. Pin connections P can be used to form connections between upper bone part B1 with upper ring 11. Similarly, pin connectors P can be used to form a connection between bone part B2 and lower ring 18. Such pin connectors P for interfacing between a ring or plate and a bone part are well known in the art. In FIGS. 1 and 5, bone parts B1 and B2 represent proximal and distal end portions of a patient's long bone that has been fractured at fracture site F.

Lower ring 18 is similarly configured to correspond to the ring 11, providing a central opening, inner and outer annular surfaces, and upper and lower surfaces. The lower ring 18 provides a plurality of circumferentially spaced apart openings or slots 17 so that the lower ends of the struts 19–24 can be attached thereto using universal joints and bolted connections.

In FIGS. 1 and 7, the lower end portion of each of the support struts 19–24 is shown attached to lower ring 18. A plurality of universal joints 25 are mounted respectively at the lower end portion of each of the support struts 19–24. Bolted connections 26 can be used for bolting each of the universal joints 25 to the ring 18 as shown in FIG. 1. In such a case, a bolt of the bolted connection 26 passes through one of the circumferentially spaced openings or slots 17 in ring 18. The upper end portion of each of the support struts 19–24 is also provided with a universal joint 39 that is part of a position adjusting member 27.

Each position adjusting member (see FIG. 4) includes a frame or bracket 28 that is substantially T-shaped having a longitudinal flange 29 and a transverse flange 30 mounted at the end portion of the longitudinal flange 29 opposite upper ring 11. Threaded rods 31, 32 are positioned in between upper ring 11 and transverse flange 30 portion of bracket 28.

Each position adjusting member 27 has a pair of internally threaded spools 33, 34 mounted respectively upon threaded rods 31, 32.

Figure 4:
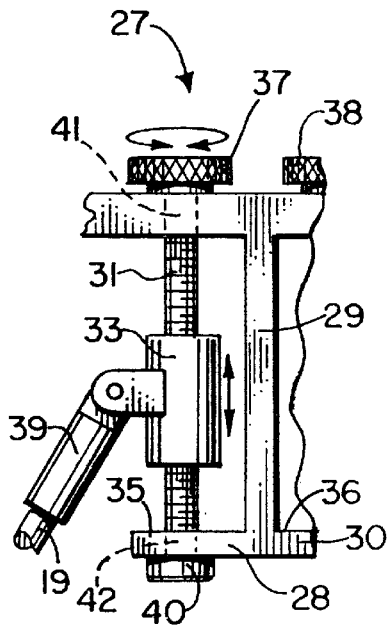
FIG. 4 is a fragmentary top view of the preferred embodiment of the apparatus of the present invention illustrating the position adjusting member portion thereof.
Figure 3:
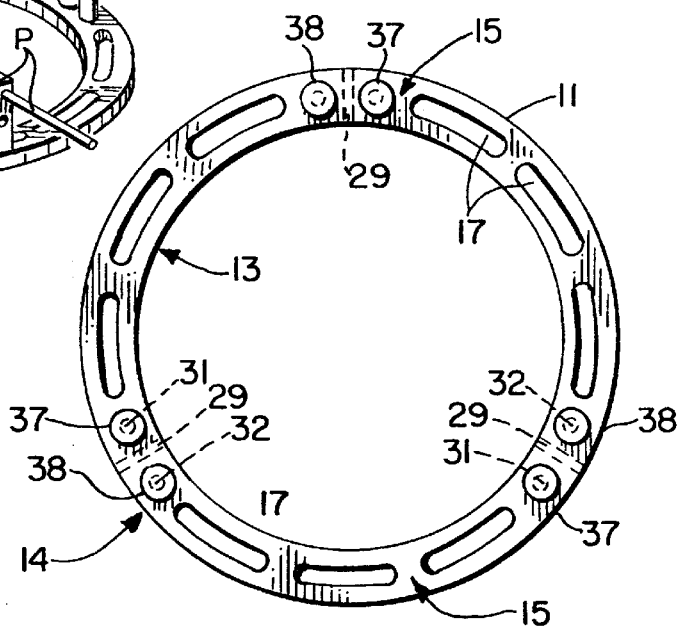
FIG. 3 is a fragmentary top view of the preferred embodiment of the apparatus of the present invention illustrating the upper ring portion thereof.

Transverse flange 30 provides a pair of spaced apart bearing surfaces 35, 36. A lower end portion of each of the threaded rods 31, 32 is mounted on the respective bearing surfaces 35, 36 with an annular stop member 40 as shown in FIG. 4. The other end portion of each of the threaded rods 31, 32 extends through an opening or slot 17 of ring 11. Each rod 31, 32 is affixed to a knob 37, 38 respectively for rotation therewith.

Each rod 31, 32 has unthreaded cylindrically-shaped end portions that are designated as 41, 42 in FIG. 4. In this fashion, any of the support struts 19–24 can be moved toward or away from the upper ring 11 by rotation of the selected knob 37, 38 of the position adjusting member 27.

Turning the selected knob 37 or 38 will raise or lower the spools 33, 34 which in turn changes the vertical position of the upper universal joints 39 as shown by arrow 43 in FIG. 4. Because the supports struts 19–24 have a fixed length, the lower universal joints 25 will move in order to change the angular position of the lower ring 18 relative to the upper ring 11.

FIGS. 5 and 6 show an alternate embodiment of the apparatus of the present invention that is designated by the numeral 50 in FIG. 5. Fixation frame apparatus 50 is a unilateral fixator that uses a pair of spaced apart rods 53, 54. Rods 53, 54 are positioned along an axial line that is generally parallel to the bone shown in FIG. 5 in the form of two bone parts B1, B2 separated at fracture site F.

In FIG. 5, the bone part B1 is shown having a bone pin 51 attached thereto in a manner known in the art. Similarly, the bone part B2 is shown having bone pin 52 attached thereto. These spaced apart upper and lower respective bone pins 51, 52 form an attachment to the bone parts B1, B2 respectively that enables the fixation frame apparatus 50 of the present invention to hold the bone parts 51, 52 in a desired fixed position with respect to each other. The apparatus 50 of the present invention can be used for example to gradually increase the space between bone pins 51, 52 such as during an Ilizarov-type surgical procedure that is used to increase the length of the bone that is comprised of bone parts B1 and B2 in FIG. 5. In such a case, clamps 55, 56 gradually move the plates 57, 58 apart.

Bone pin 51 is attached to upper pin clamp 55, a commercially available clamp apparatus. Similarly, bone pin 52 attaches to clamp 56 that is also commercially available. The clamp 55 is secured to upper rod 53 that is attached to the center of upper plate 57. The lower rod 54 similarly attaches to the center of plate 58. Rods 53, 54 can be elongated linear rods, each having a hexagonal cross section, for example.

A plurality of longitudinally extending struts 59–64 span in between the plates 57, 58 as shown in FIG. 5. The upper end of each of the struts 59–64 is attached to a position adjusting member 27 that is constructed in accordance with the above discussion of the preferred embodiment and FIGS. 1–4 of the drawings.

Each position adjusting member 27 includes bracket 28, longitudinal flange 29, transverse flange 30, a pair of threaded rods 31, 32, spools 33, 34, and adjustment knobs 37, 38. Universal joints 39 are used as an interface between the upper end of each of the struts 59–64 and the respective threaded rod 31 or 32 of the position adjusting member 27. Upper plate 57 has openings that accept the upper end of the rods 31, 32 as shown in FIGS. 4 and 5.

The lower end of each of the struts 59, 64 forms an attachment to plate 58 as shown more particularly in FIGS.

5 and 6. In FIG. 6, a single strut 59 is shown, its lower end forming a connection with plate 58. The lower end of strut 59 (and of all of the struts 59–64) can have an externally threaded end portion 66 that forms an attachment with ball 66 at internally threaded socket 67.

Plate 67 provides a spherically-shaped opening 68 for receiving ball 66 as shown in FIG. 6. Retainer plate 69 fits cylindrically-shaped socket 70 at the lower surface of plate 58. Bolted connections 71 can be used to secure retainer plate 68 to cylindrically-shaped socket 70 and plate 58 as shown in FIG. 6. Plate 69 can have a dished or concave surface 72 that conforms to the shape of ball 66 as shown in FIG. 6.

The following table lists the parts numbers and parts descriptions as used herein and in the drawings attached hereto.

PARTS LIST

| Part Number | Description |
| --- | --- |
| 10 | fixation frame apparatus |
| 11 | upper frame apparatus |
| 12 | central opening |
| 13 | inner annular surface |
| 14 | outer annular surface |
| 15 | upper surface |
| 16 | lower surface |
| 17 | slots |
| 18 | lower ring |
| 19 | support strut |
| 20 | support strut |
| 21 | support strut |
| 22 | support strut |
| 23 | support strut |
| 24 | support strut |
| 25 | universal joint |
| 26 | bolted connection |
| 27 | position adjusting member |
| 28 | bracket |
| 29 | longitudinal flange |
| 30 | transverse flange |
| 31 | threaded rod |
| 32 | threaded rod |
| 33 | spool |
| 34 | spool |
| 35 | bearing surface |
| 36 | bearing surface |
| 37 | knob |
| 38 | knob |
| 39 | universal joint |
| 40 | annular stop member |
| 41 | unthreaded rod end portion |
| 42 | unthreaded rod end portion |
| 43 | arrow |
| 50 | fixation frame apparatus |
| 51 | bone pin |
| 52 | bone pin |
| 53 | upper rod |
| 54 | lower rod |
| 55 | upper pin clamp |
| 56 | lower pin clamp |
| 57 | upper plate |
| 58 | lower plate |
| 59 | strut |
| 60 | strut |
| 61 | strut |
| 62 | strut |
| 63 | strut |
| 64 | strut |
| 65 | threaded end |
| 66 | ball |
| 67 | internally threaded socket |
| 68 | spherically-shaped opening |
| 69 | retainer plate |

-continued

PARTS LIST

| Part Number | Description |
| --- | --- |
| 70 | cylindrically-shaped socket |
| 71 | bolted connection |
| 72 | dished surface |
| B1 | bone part |
| B2 | bone part |
| F | fracture site |
| P | pin connector |

The foregoing embodiments are presented by way of example only; the scope of the present invention is to be limited only by the following claims.

What is claimed is:

1. An orthopaedic fixation apparatus comprising:

a) an upper ring having a central opening, inner and outer ring surfaces and upper and lower ring surfaces;

b) a lower ring having a central opening, inner and outer ring surfaces and upper and lower ring surfaces;

c) a plurality of struts that span between the rings for holding the rings apart in desired ring positions;

d) a plurality of position adjusting members that each form an interface between one of the rings and one end of one of the struts, each position adjusting member having end portions, one end portion forming a connection to a ring, the other end portion being connected to a strut;

e) each position adjusting member having an articulating connecting portion that forms an interface between an end of a strut and a ring; and g) wherein each of the position adjusting members is configured to increase the distance between one end of a strut and one of the rings.

2. The orthopaedic fixation apparatus of claim 1 wherein the struts are of substantially the same length.

3. The orthopaedic fixation apparatus of claim 1 wherein there are six struts.

4. The orthopaedic fixation apparatus of claim 1 wherein a plurality of the position adjusting members are positioned next to one of the rings.

5. The orthopaedic fixation apparatus of claim 1 wherein all of the position adjusting members are positioned next to one of the rings.

6. The orthopaedic fixation apparatus of claim 1 wherein each of the position adjusting members includes an adjustment knob that is rotated to vary the distance between a ring and a strut.

7. The orthopaedic fixation apparatus of claim 1 wherein each of the rings has a plurality of ring openings that extend between respective ring upper and lower surfaces, and wherein an end portion of a position adjusting member forms a connection to a ring at a ring opening.

8. An orthopaedic fixation apparatus comprising:

a) an upper ring having a central opening, inner and outer ring surfaces and upper and lower ring surfaces;

b) a lower ring having a central opening, inner and outer ring surfaces and upper and lower ring surfaces;

c) a plurality of struts that span between the rings for holding the rings apart in desired ring positions;

d) a plurality of position adjusting members that form an interface between one of the rings and one end of the struts, each position adjusting member having end portions, one end portion forming a connection to a ring, the other end portion being positioned in between the upper and lower rings;

e) each position adjusting member having an articulating portion that attaches to an end of a strut; and f) wherein the position adjusting members are configured to increase the distance between one end of a strut and one of the rings;

g) wherein each of the position adjusting members includes a rotatable threaded rod and the articulating portions travels upon the threaded rod.

9. The orthopaedic fixation apparatus of claim 8 wherein each of the rings has a plurality of ring openings that extend between respective ring upper and lower surfaces, and wherein an end portion of a position adjusting member forms a connection to a ring at a ring opening.

10. An orthopaedic fixation apparatus comprising:

a) an upper ring having a central opening, inner and outer ring surfaces and upper and lower ring surfaces;

b) a lower ring having a central opening, inner and outer ring surfaces and upper and lower ring surfaces;

c) a plurality of struts that span between the rings for holding the rings apart in desired ring positions;

d) a plurality of position adjusting members that form an interface between one of the rings and one end of the struts, each position adjusting member having end portions, one end portion forming a connection to a ring, the other end portion being positioned in between the upper and lower rings;

e) each position adjusting member having an articulating portion that attaches to an end of a strut; and f) wherein the position adjusting members are configured to increase the distance between one end of a strut and one of the rings;

g) wherein each position adjusting member includes an adjustment knob that is rotated to vary the distance betweem the ring and a strut;

h) wherein each of the position adjusting members includes a rotatable threaded rod and the articulating portions each travel upon a threaded rod.

11. The orthopaedic fixation apparatus of claim 10 wherein the articluating portion is a universal joint that forms an interface between a strut and a threaded rod.

12. The orthopaedic fixation apparatus of claim 10 wherein each of the rings has a plurality of ring openings that extend between respective ring upper and lower surfaces, and wherein an end portion of a position adjusting member forms a connection to a ring at a ring opening.

13. An orthopaedic fixation apparatus comprising:

a) an upper ring having a central opening, inner and outer ring surfaces and upper and lower ring surfaces;

b) a lower ring having a central opening, inner and outer ring surfaces and upper and lower ring surfaces;

c) a plurality of struts that span between the rings for holding the rings apart in desired ring positions;

d) a plurality of position adjusting members that form an interface between one of the rings and one end of the struts, each position adjusting member having end portions, one end portion forming a connection to a ring at a ring opening, the other end portion being positioned in between the upper and lower rings;

e) each position adjusting member having an articulating portion that attaches to an end of a strut; and f) wherein the position adjusting members are configured to increase the distance between one end of a strut and one of the rings; and g) wherein each position adjusting member comprises:

a support bracket member;

a threaded rod having a helical thread thereon, one end of the rod abutting the frame, the other end of the rod extending through one of the openings;

a universal joint with an internally threaded sleeve that is mounted on the rod;

a know that enables a user to rotate the rod;

wherein rotation of the knob and moves the universal joint into multiple adjustment positions in between the ring and the support bracket.

14. The orthopaedic fixation apparatus of claim 13 wherein each of the rings has a plurality of ring openings that extend between respective ring upper and lower surfaces, and wherein an end portion of a position adjusting member forms a connection to a ring at a ring opening.

15. An orthopaedic fixation apparatus comprising:

a) an upper ring having a central opening, inner and outer ring surfaces and upper and lower ring surfaces;

b) a lower ring having a central opening, inner and outer ring surfaces and upper and lower ring surfaces;

c) a plurality of struts of fixed length that span between the rings for holding the rings apart in desired ring positions, one end of each strut attaching to one of the rings with a universal joint;

d) a plurality of position adjusting members that form an interface between one of the rings and one end of the struts, each position adjusting member having end portions, one end portion forming a connection to a ring, the other end portion being positioned in between the upper and lower rings;

e) each position adjusting member having an articulating connecting portion that forms an interface between an end of a strut and a ring; and f) wherein the position adjusting members are configured to increase the distance between one end of a strut and one of the rings.

16. The orthopaedic fixation apparatus of claim 15 wherein each of the rings has a plurality of ring openings that extend between respective ring upper and lower surfaces, and wherein an end portion of a position adjusting member forms a connection to a ring at a ring opening.

17. The orthopaedic fixation apparatus of claim 15 wherein each strut has ends with respective universal joints attached thereto, one of the universal joints defining the articulating member.

18. An orthopaedic fixation apparatus comprising:

a) an upper ring having a central opening, inner and outer ring surfaces and upper and lower ring surfaces;

b) a lower ring haivng a central opening, inner and outer ring surfaces and upper and lower ring surfaces;

c) a plurality of struts of fixed length that span between the rings for holding the rings apart in desired ring positions, one end of each strut attaching to one of the rings with a universal joint;

d) a plurality of position adjusting members that form an interface between one of the rings and one end of the struts, each position adjusting member having end portions, one end portion forming a connection to a ring, the other end portion being positioned in between the upper and lower rings;

e) each position adjusting member haivng an articulating portion that atatches to an end of a strut; and f) wherein the position adjusting members are configured to increase the distance between one end of a strut and one of the rings; and g) wherein each position adjusting member includes a bracker that is mounted on a ring and extends a partial distance to another ring and a rod member supported by the combination of the ring and bracket, the rod being rotatable, and an articulating member travelling upon the rod between rod ends responsive to a rotation of the rod.

19. The orthopaedic fixation apparatus of claim 18 wherein each of the rings has a plurality of ring openings that extend between respective ring upper and lower surfaces, and wherein an end portion of a position adjusting member forms a connection to a ring at a ring opening.

20. An orthopaedic fixation apparatus comprising:
   a) an upper support member having a periphery and upper and lower surfaces;
   b) a lower support member having a periphery and upper and lower surfaces;
   c) a plurality of struts that span between the support members for holding them apart in desired positions relative to one another;
   d) a plurality of position adjusting members that form an interface between one of the support members and one end of the struts, each position adjusting member having end portions, one end portion forming a connection to a support member at an opening, the other end portion being positioned in between the upper and lower support members;
   e) each position adjusting member having an articulating connecting portion that forms an interface between an end of a strut and a support member; and
   f) wherein the position adjusting members are configured to increase the distance between one end of a strut and one of the support members.

21. The orthopaedic fixation apparatus of claim 20 wherein the struts are of substantially the same length.

22. The orthopaedic fixation apparatus of claim 20 wherein a plurality of the position adjusting members are positioned next to one of the support members.

23. The orthopaedic fixation apparatus of claim 20 wherein all of the position adjusting members are connected to one of the support members.

24. The orthopaedic fixation apparatus of claim 20 wherein each of the position adjusting members includes an adjustment knob that is rotated to vary the distance between a support member and a strut.

25. An orthopaedic fixation apparatus of claim 20 wherein each of the rings has a plurality of ring openings that extend between respective ring upper and lower surfaces, and wherein an end portion of a position adjusting member forms a connection to a ring at a ring opening.

26. An orthopaedic fixation apparatus comprising:
   a) an upper support member having a periphery and upper and lower surfaces;
   b) a lower support member having a periphery and upper and lower surfaces;
   c) a plurality of struts that span between the support members for holding them apart in desired positions relative to one another;
   d) a plurality of position adjusting members that form an interface between one of the support members and one end of the struts, each position adjusting member having end portions, one end portion forming a connection to a support member, the other end portion being positioned in between the upper and lower support members;
   e) each position adjusting member having an articulating portion that attaches to an end of a strut; and
   f) wherein the position adjusting members are configured to increase the distance between one end of a strut and one of the support members; and
   g) wherein each of the position adjusting members includes a rotatable threaded rod and the articulating portions travel upon the threaded rod.

27. The orthopaedic fixation apparatus of claim 26 wherein each of the rings has a plurality of ring openings that extend between respective ring upper and lower surfaces, and wherein an end portion of a position adjusting member forms a connection to a ring at a ring opening.

28. An orthopaedic fixation apparatus comprising:
   a) an upper support member having a periphery and upper and lower surfaces;
   b) a lower support member having a periphery and upper and lower surfaces;
   c) a plurality of struts that span between the support members for holding them apart in desired positions relative to one another;
   d) a plurality of position adjusting members that form an interface between one of the support members and one end of the struts, each position adjusting member having end portions, one end portion forming a connection to a support member, the other end portion being positioned in between the upper and lower support members;
   e) each position adjusting member having an articulating portion that attaches to an end of a strut; and
   f) wherein the position adjusting members are configured to increase the distance between one end of a strut and one of the support members; and
   g) wherein each of the position adjusting members includes a rotatable threaded rod and the articulating portions each travel upon one of the threaded rods.

29. The orthopaedic fixation apparatus of claim 28 wherein the articulating portion is a universal joint that forms an interface between a strut and a threaded rod.

30. The orthopaedic fixation apparatus of claim 20 wherein each of the rings has a plurality of ring openings that extend between respective ring upper and lower surfaces, and wherein an end portion of a position adjusting member forms a connection to a ring at a ring opening.

31. An orthopaedic fixation apparatus comprising:
   a) sn upper ring having a central opening, inner and outer ring surfaces and upper and lower ring surfaces;
   b) a lower ring having a central opening, inner and outer ring surfaces and upper and lower ring surfaces;
   c) a plurality of struts that span between the rings for holding the rings apart in desired ring positions;
   c) a plurality of position adjusting members that form an interface between one of the rings and one of the struts, each position adjusting member having end portions, one end portion forming a connection to a ring, the other end portion being positioned in between the upper and lower rings;
   e) each position adjusting member having an articulating portion that attaches to an end of a strut; and
   f) wherein the position adjusting members are configured to increase the distance between one end of a strut and one of the rings wherein each position adjusting member comprises:
   a support bracket member;

a threaded rod having a helical thread thereon one end of the rod abutting the frame, the other end of the rod extending through one of the openings;

a universal joint with an internally threaded sleeve that is mounted on the rod;

a knob that enables a user to rotate the rod; and wherein rotation of the knob and the rod moves the universal joint into multiple adjustment positions in between the ring and the support bracket.

32. An orthopaedic fixation apparatus comprising:
   a) an upper support member and upper and lower surfaces;
   b) a lower support member having upper and lower support member surfaces;
   c) a plurality of struts of fixed length that span between the support members for holding them apart in desired positions relative to one another, one end of each strut attaching to one of the with pivoting joint;
   d) a plurality of position adjusting members that form an interface between one of the support members and one end of each of the struts, each position adjusting member having end portions, one end portion forming a connection to a supporting member, the other end portion being positioned in between the upper and lower support members;
   e) each position adjusting member having a joint articulating connecting portion that forms an interface between an end of a strut and a support member; and
   f) wherein the position adjusting members are configured to increase the distance between one end of a strut and one of the support members.

33. The orthopaedic fixation apparatus of claim 32 wherein each strut has ends with respective universal joints attached thereto, one of the universal joints defining the articulating member.

34. An orthopaedic fixation apparatus comprising:
   a) an upper support member and upper and lower surfaces;
   b) a lower support member having upper and lower support member surfaces;
   c) a plurality of struts of fixed length that span between the support members for holding them apart in desired positions relative to one another, one end of each strut attaching to one of the with a pivoting joint;
   d) a plurality of position adjusting members that from an interface between one of the support members and one end of each of the struts, each position adjusting member having end positions, one end portion forming a connection to a support member, the other end portion being positioned in between the upper and lower support members;
   e) each position adjusting member having a joint articulating portion that attaches to an end of a strut; and
   f) wherein the position adjusting members are configured to increase the distance between one end of a strut and one of the support members; and
   g) wherein each position adjusting member includes a bracket that is mounted on one support member and extends a partial distance toward the other support member and a rod member supported by the combination of the support member and bracket the rod being rotatable, and a spool member travelling upon the rod between rod ends responsive to a rotation of the rod.

* * * * *

UNITED STATES PATENT AND TRADEMARK OFFICE
CERTIFICATE OF CORRECTION

PATENT NO.   : 6,129,727
DATED        : October 10, 2000
INVENTOR(S)  : Ed Austin, Anthony James and James E. Orsak It is certified that error appears in the above-identified patent and that said Letters Patent is hereby corrected as shown below:

<u>Title page,</u>
Item [73], "Assignee: Smith & Nephew, Memphis, Tenn." be changed to -- Assignee: Smith & Nephew, Inc., Memphis, Tenn. --

Signed and Sealed this

Twenty-fifth Day of June, 2002

*Attest:*

*Attesting Officer*

JAMES E. ROGAN
*Director of the United States Patent and Trademark Office*